United States Patent [19]

Gesser et al.

[11] Patent Number: 5,017,731
[45] Date of Patent: May 21, 1991

[54] DIRECT CONVERSION OF ETHANE TO ALCOHOLS BY HIGH PRESSURE CONTROLLED OXIDATION

[76] Inventors: Hyman D. Gesser, 218 Girton Blvd., Winnipeg Man., Canada, R3P OA7; Norman R. Hunter, Grp. 4 Box 16, R.R. 1, St., St. Norbert, MB, Canada; Prasad S. Yarlagadda, 19-A Camelot Ct., Buffalo, N.Y. 14214; Lawrence A. Morton, 19 Temple Bay, Winnipeg, Manitoba, Canada, R3T 2V1

[21] Appl. No.: 534,310

[22] Filed: Jun. 5, 1990

Related U.S. Application Data

[63] Continuation of Ser. No. 166,013, Mar. 9, 1988, abandoned.

[30] Foreign Application Priority Data

Mar. 13, 1987 [NZ] New Zealand .................. 219621

[51] Int. Cl.$^5$ .................. C07C 29/50; C07C 31/08; C07C 31/04
[52] U.S. Cl. .................. 568/910; 44/451; 44/452
[58] Field of Search .................. 568/910

[56] References Cited

U.S. PATENT DOCUMENTS 3,092,667  6/1963  Murphy .................. 568/910
4,137,256  1/1979  Slattery et al. .................. 260/502 A
4,618,732  10/1986  Gesser et al. .................. 568/910

OTHER PUBLICATIONS

Newitt et al, Proc. Roy. Soc. (London), Slow Oxidations at High Pressures I Methane and Ethane, Ser. A. 147, pp. 555-510(1934).

*Primary Examiner*—J. E. Evans
*Attorney, Agent, or Firm*—Ezra Sutton

[57] ABSTRACT

A process directly converting ethane to ethanol and methanol uses controlled oxidation. The reaction takes place in an inert reactor, i.e., one having internal surfaces which do not affect the reaction, in the absence of a catalyst. The ethane is intimately mixed with air or oxygen prior to the introduction of the mixed gases into a heated pre-reactor which allows the pre-reaction or induction period to proceed. The pre-reacted gases then enter the reactor where the reaction takes place at elevated temperatures of 200° to 350° and at elevated pressure of from 10 to 150 atmospheres. The percentage of oxygen in the mixture of reactant gases is kept below 15% by volume and is preferably 2 to 10% by volume. Apparatus for carrying out the method is also described.

3 Claims, 5 Drawing Sheets

DIRECT CONVERSION OF ETHANE TO ALCOHOLS BY HIGH PRESSURE CONTROLLED OXIDATION

This application is a continuation of application Ser. No. 166,013, filed Mar. 9, 1988, now abandoned.

BACKGROUND OF THE INVENTION

I. Field of the Invention

This invention relates to the controlled oxidation of ethane to produce primarily ethanol with some methanol and little or no aldehyde or acid.

II. Description of Prior Art

This invention relates to the direct conversion of ethane to ethanol (Direct Ethane Oxidation, DEO). Ethanol ($C_2H_5OH$) is presently produced either by the fermentation of sugar (Reaction 1) or by the hydration of ethylene (Reaction 2) which is normally formed by the dehydrogenation of ethane (Reaction 2a).

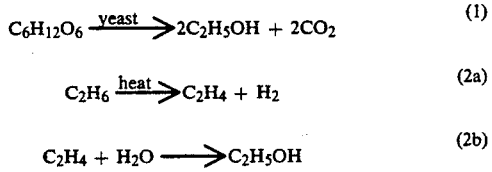

The ethanol cost from these two processes are estimated to be $1.67 and $1.38 US/gal respectively.

Other processes have been described which include the hydrogenation of acetic acid (by Humphreys and Glasgow) and the hydrogenolysis of methyl acetate (by Halcon SD). Ethanol from these two processes is estimated to cost $1.06 and $1.15 US/gal respectively.

Ethane is a by-product recovered from natural gas in the liquified petroleum gas fraction along with propane and butane. Ethane is primarily used to make ethylene (via Reaction 2a) which is used to produce the plastic-polyethylene (polythene). There is presently a surplus of ethane on the world market and it is used as a fuel for its heat value. The estimated cost of ethanol via the DEO process of this invention is approximately $0.53 US/gal which makes it an attractive octane enhancer for gasoline.

Previous attempts to convert ethane directly into ethanol by partial oxidation met with limited success (Newitt and Block, Proceedings of Royal Society, Vol. 140A, p. 426, 1933; Newitt and Szego, Proceedings of Royal Society Vol. 147A, p. 555, 1934; Bell et al, Industrial and Engineering Chemistry Vol. 41, pg. 2609-12, 1949; Shlau and Albright, Industrial and Engineering Chemistry—Process Development Vol. 21, p. 101, 1982).

Only the early workers, Newitt and coworkers, obtained ethanol in significant yields (20 to 60%).

One of the neglected aspects of the oxidation process is the induction period which Bone and Hill (Proceedings of the Royal Society Vol 129A, p. 434, 1930) showed in a static system to decrease with increase in temperature and increase in pressure. In plug flow reactor system this induction period must be dealt with by the use of a pre-heater.

Accordingly, the object of the invention is to provide a process for the direct conversion of ethane to ethanol which is relatively easy to operate and which gives a good yield of alcohol with high selectivity.

B. SUMMARY OF INVENTION

One aspect of the invention provides a process for the direct conversion of ethane to ethanol. This is achieved by reacting ethane with oxygen or air in the absence of a catalyst in an inert reactor at an elevated temperature and pressure.

Another aspect of the invention provides a means of allowing the induction period, which precedes the oxidation reaction, to be of short duration thereby permitting the reaction to proceed in the heated zone of the reactor. This multi-zone furnace overcomes the difficulties experienced by previous workers and leads to larger through-put of reactants i.e, faster flow rates.

Another aspect of the invention is the absence of a catalyst which usually destroys the desired product. Hence, by carrying out the reaction in a homogeneous gas phase system using a plug flow reactor, the products, once formed, can be readily removed from the heated zone and prevented from reacting further.

C. DESCRIPTION OF THE DRAWINGS

D. DESCRIPTION OF THE PREFERRED EMBODIMENT

Our experiments were conducted in an apparatus similar to that recently described by Gesser et al. U.S. Pat. No. 4,618,732 (issued Oct. 21, 1986 the contents of which are incorporated herein by reference. The high pressure apparatus consisted of dual flow lines which allowed the $O_2$ and $C_2H_6$ to be mixed in a Teflon packed cross fitting prior to entering the reactor which consisted of a glass (Pyrex) lined high pressure steel tube heated electrically and thermostatically controlled to any desired temperature (100° to 500° C.). At least two such heaters were required. A pre-heater, which was controlled and monitored independently of the furnace heater, allowed the gases to pass through the induction period by the time the gases entered the reaction zone. The temperature of each heater was determined by the experimental parameters, namely pressure, flow rate (residence time), $O_2$ concentration, and furnace lengths. In order to ensure that the flow of the gases was unidirectional, check valves were installed in the gas lines the mixing cross. The exit to the reactor was throttled by a vernier needle valve which brought the gases and products to atmospheric pressure through a heated capillary tube which led to an 8-port gas chromatography gas sampling valve.

A gas chromatograph with a thermal conductivity detector was used to analyse the gases for $CH_4$, $N_2$, $C_2H_6$, $CO$, $CO_2$, methanol, ethanol, and water. The liquid products were also collected by being trapped at −78° C. as they exited the reactor and were analysed by gas chromatography and confirmed by G.C.-mass spectrometry.

The results can be divided into two groups; the low pressure runs with P<50 atm and the high pressure experiment with P>50 atm where the ethane cylinder and connecting lines to the reactor had to be heated to obtain pressures greater than the critical pressure of ethane ($P_c$=48.8 atm, $T_c$=32° C.). In practice, liquid ethane can be injected into the pre-reactor where it is intimately mixed with oxygen.

Figure 1:
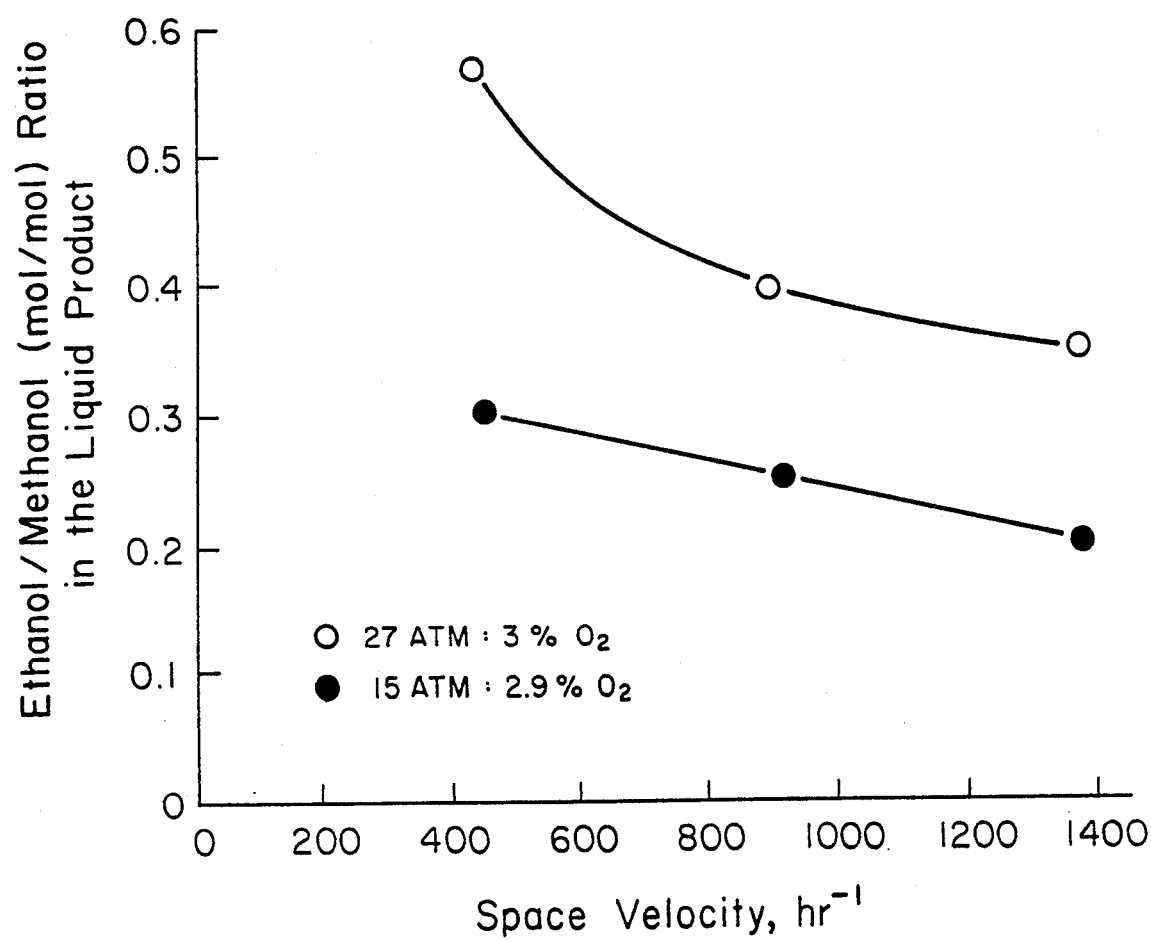
FIG. 1, is a graph showing the ratio of ethanol/methanol in the products as a function of space velocity and pressure.
Figure 2:
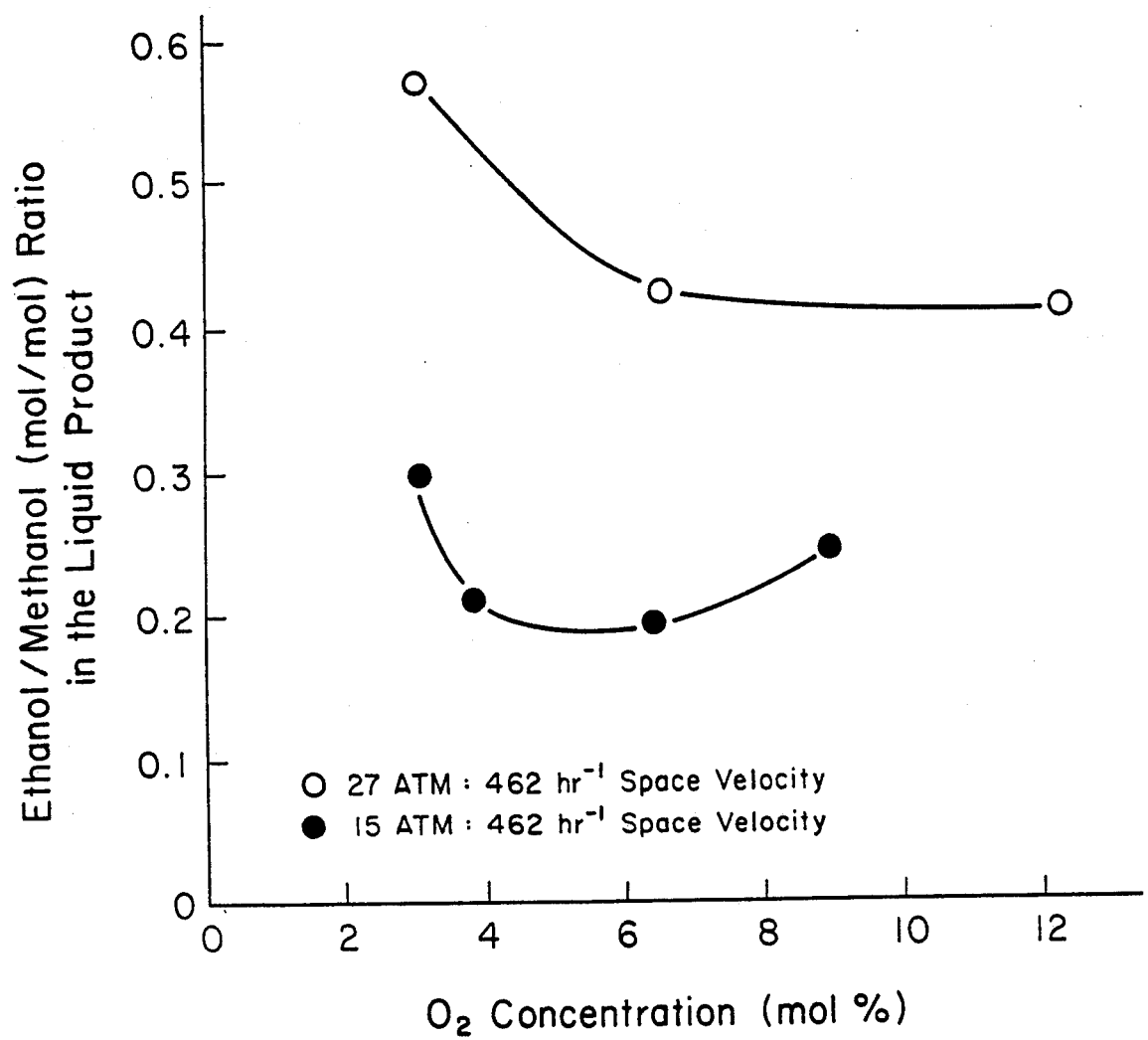
FIG. 2 is a graph showing the ratio of ethanol/methanol in the products as a function of oxygen concentration and pressure.
Figure 3:
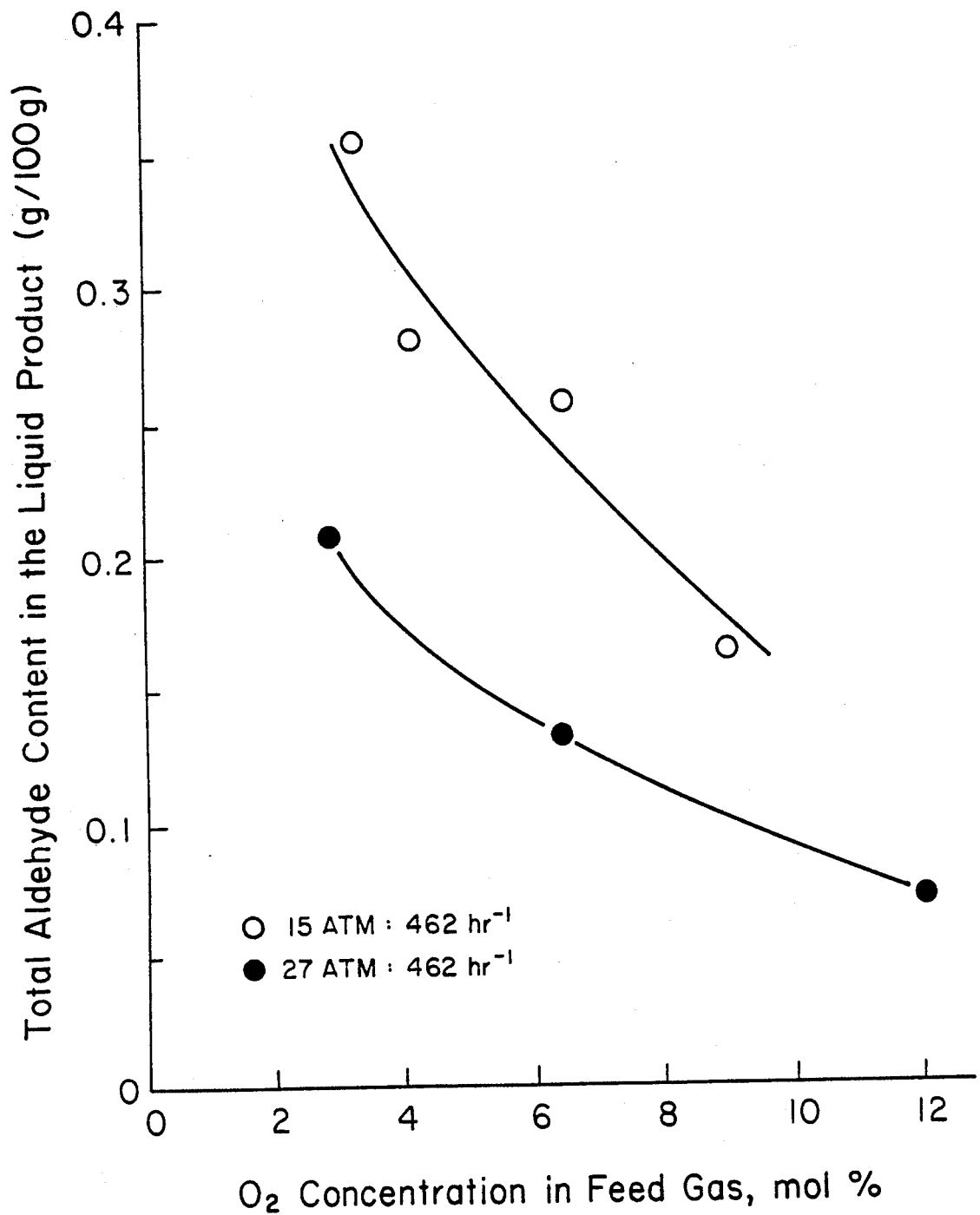
FIG. 3 is a graph showing the concentration of aldehyde in the liquid product as a function of pressure and $O_2$ concentration.

The low pressure results (Table 1) clearly show that a lower space velocity increases the ratio of ethanol to methanol (FIG. 1). Higher values of this ratio are also favoured at lower $O_2$ concentrations (FIG. 2). Aldehydes, which were also formed in the reaction were detected during the gas chromatographic analysis of the liquid product and showed lower yields at higher pressures and higher $O_2$ concentrations (see FIG. 3). The conversions were estimated by the liquid products collected and in the case of experiment #204 (Table 1), the conversion was also calculated (8%) by the use of nitrogen from the air present as an internal standard. The maximum conversion of $C_2H_6$ is based on the

$$C_2H_6 + \tfrac{1}{2}O_2 \rightarrow C_2H_5OH \quad (3)$$

reaction and is 2×$O_2$ consumed whereas the minimum conversion based on complete oxidation

$$C_2H_6 + \tfrac{7}{2}O_2 \rightarrow 2CO_2 + 3H_2O \quad (4)$$

would be 2/7×$O_2$ consumed or 0.28×$O_2$ consumed.

The results of the on-line analysis of the product stream for several experiments are given in Table 2 and show that the water content is significantly lower than that found in the liquid product sample. This is usually the case for water which is difficult to determine quantitatively in a gas stream. The composition of the liquid determined by direct analysis is probably more reliable.

Figure 4:
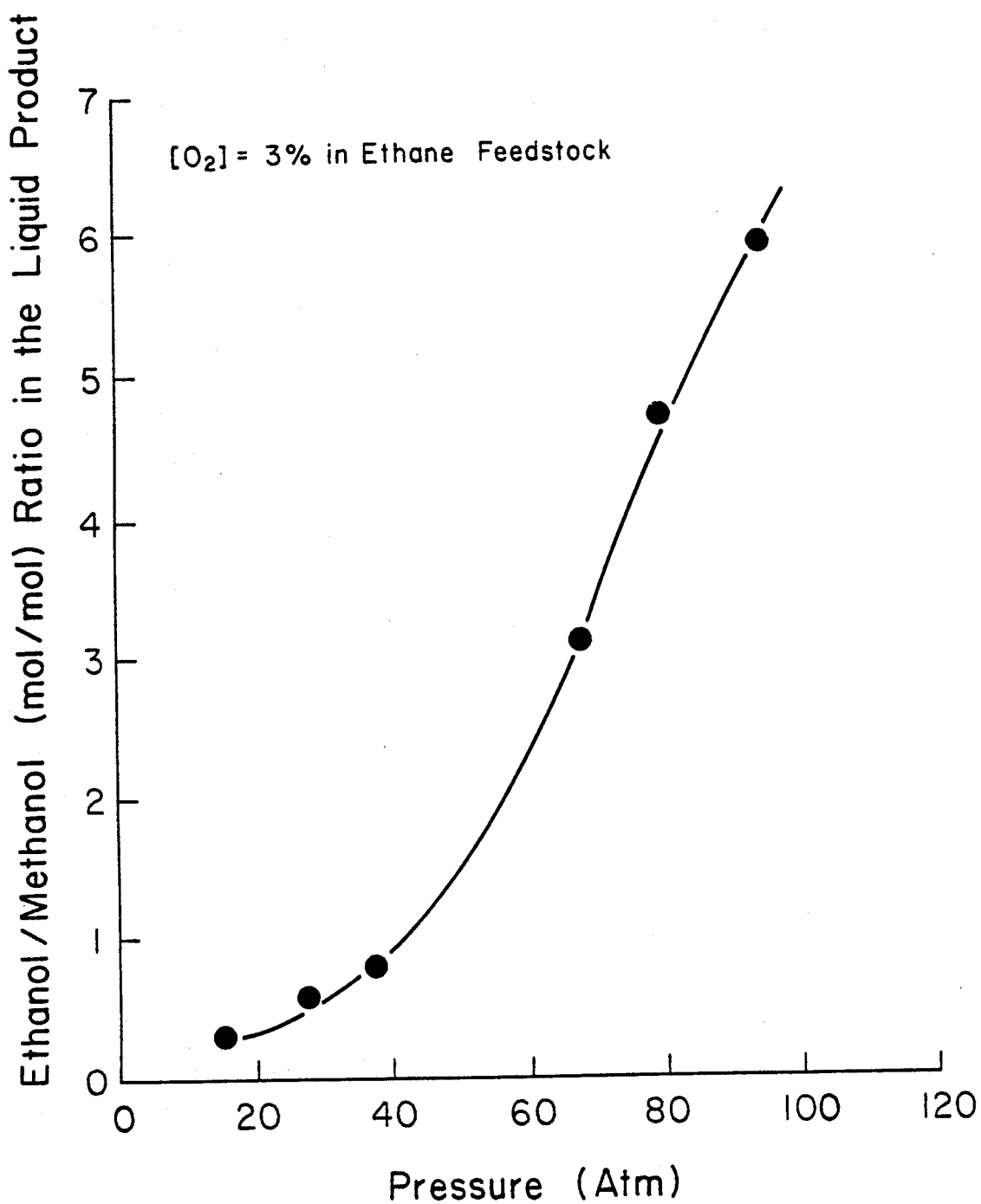
FIG. 4 is a graph showing the ratio of ethanol/methanol in the products as a function of pressure at 3% $O_2$ and constant flow of 100 mL/min (NTP).

The value of the ethanol/methanol ratio determines the viability of the process and by increasing the reaction pressure to almost 100 atm it was possible to obtain values of this ratio of about 6 (see FIG. 4). It must be noted that the data in FIG. 4 were obtained under constant reactant flow of 100 mL/min NTP. This implies that the actual residence time of the reaction mixture has gone from about 1 min at 15 atm (284° C.) to about 7 min at 90 atm (236° C.) (Table 3).

Figure 5:
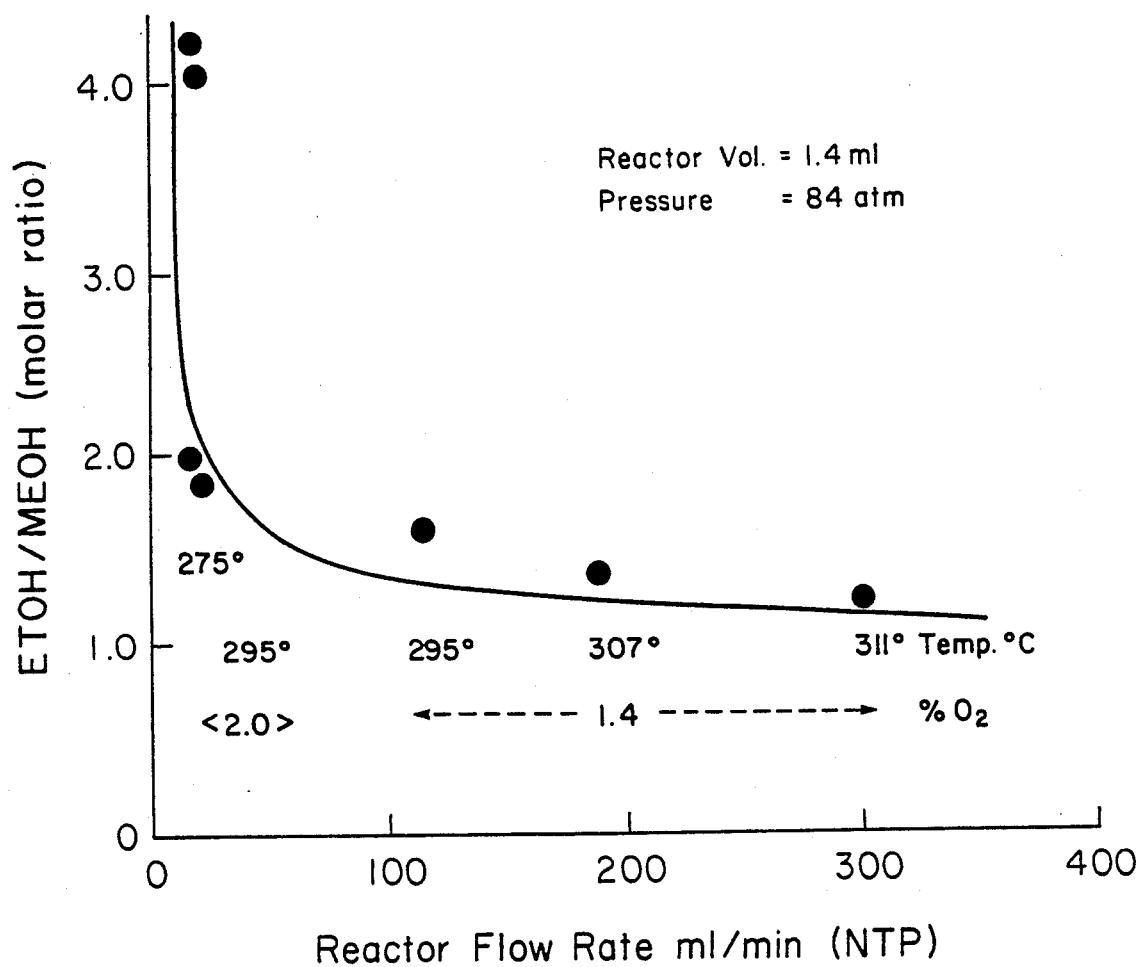
FIG. 5 is a graph showing the ratio of ethanol to methanol in the products as a function of flow rate at pressures of 85±5 atm and about 1.5% $O_2$ and about 300° C.

The results showing the effect of flow rate (residence time) at high pressures (about 85 atm), and temperatures of 275° to 310° C. at about 1.5% $O_2$ is presented in FIG. 5. The lower flow rate and longer residence time gave higher values for the ethanol/methanol ratio because the induction period was allowed to proceed before reaction took place. Thus, the results in Table 4 show how small changes in the temperature of the reactor and pre-reactor can effect large changes in the products. This is due to possible cool flame characteristics of the reaction which has been observed in the partial oxidation of methane to methanol at high pressures.

The reactor material must be inert and not act as a trap for free radicals produced in the reaction. Thus, it was shown that a decrease in surface/volume ratio of the reactor favored the formation of ethanol at a lower temperature. Similarly glass walls were preferred to steel and it is possible to coat the walls with salts, waxes and plastics such as polytetrafluoroethylene (Teflon) which inhibit the recombination of free radicals and thus permit the reaction to proceed to greater conversion of ethane.

When air is used instead of oxygen in the reaction the nitrogen acts as a diluent resulting in lower conversion of the ethane. If recycling is to be effected under such conditions then the unreacted ethane in the product must be separate from the nitrogen. This can be readily done by cooling the exit gas. The savings realized by not having to use pure oxygen could more than pay for the extra costs involved in separating out the nitrogen from the ethane especially if efficient heat exchangers are used to conserve energy.

Unreacted ethane with uncondensed products such as CO and $CO_2$, can be separated from the liquid products and recycled for further reaction with oxygen or air to form more alcohols. Alternately, the $CO_2$ can be scrubbed out of the reaction stream before returning the unreacted ethane to the reactor system.

Though ethanol is a more valuable product than methanol, a blend of these oxygenated hydrocarbons could be added directly to gasoline as an octane enhancer. Examples:

Ethane was reacted with oxygen in the apparatus described and the products analysed for the reaction at 96 atm and about 2% oxygen in a reactor having a reaction volume of 1.4 mL and a flow rate of 7 mL/min (NTP). The ratio of ethanol/methanol as 5.0 when the reaction temperature was 298° C. with a pre-reaction temperature of 256° C. When the flow rate was increased to 15 mL/min the ethanol/methanol ratio did not change significantly.

In another experiment the reaction was conducted with a wider bore reactor, (reaction volume 14.3 mL) 2% $O_2$, 102 atm pressure, and a flow rate of 80 mL/min (NTP) the ethanol/methanol ratio was 2.1 when the reactor temperature was 221° C. and the re-reactor was 238° C.

When the glass liner to the above reactor was removed the reaction volume increased from 14.3 to 19 mL. Under similar reaction conditions (Pressure=102 atm and 2% $O_2$) and a flow rate of 32 mL/min (NTP) the ethanol/methanol ratio was 3.3 at a reaction temperature of 252° C. and a pre-reaction temperature of 192° C.

Since various modifications can be made to our invention as herein above described, and many apparently widely different embodiments of same made within the spirit and scope of the claims without departing from such spirit and scope, it is intended that all matter contained in the accompanying specifications shall be interpreted as illustrative only and not in a limiting sense.

TABLE 1

Summary of the reaction conditions and products obtained during the direct ethane oxidation to ethanol process (DEO). Total $O_2$ consumption. Reaction Vol. 13 mL. Flow Rate 100 mL/min (NTP).

| Experiment Number | Reaction Conditions | | | | | | Liquid Product Composition, mol %++ | | | | | |
|---|---|---|---|---|---|---|---|---|---|---|---|---|
| | Temp. °C. | Pressure atm | $O_2$ Conc. in the Feed Gas mol % | Time-on-stream h | Space Velocity $h^{-1}$ (NTP) | Moles/ 5 hr $C_2H_6$ in | $C_2H_5OH$ | $CH_3OH$ | $H_2O$ | Moles/5 hr Liquid Product out | Total Aldehyde Content g/100 g | Ethanol Methanol mol/mol |
| 203 | 284 | 14.9 | 2.90 | 9.6 | 462 | 1.21 | 10.5 | 35.1 | 54.4 | 0.0470 | 0.355 | 0.300 |
| 201 | 309 | 14.8 | 3.85 | 5.0 | 462 | 1.20 | 8.0 | 38.0 | 54.0 | 0.0573 | 0.282 | 0.211 |
| 200 | 310 | 14.9 | 6.30 | 5.0 | 462 | 1.17 | 6.3 | 32.3 | 61.4 | 0.1521 | 0.258 | 0.195 |
| 202 | 314 | 14.7 | 8.80 | 5.0 | 462 | 1.14 | 8.3 | 33.7 | 58.0 | 0.1731 | 0.164 | 0.246 |
| 205 | 293 | 15.3 | 2.90 | 5.0 | 924 | 2.30 | 9.5 | 37.9 | 52.6 | 0.1147 | 0.343 | 0.251 |
| 206 | 294 | 16.1 | 2.90 | 4.3 | 1386 | 3.15 | 8.2 | 40.7 | 51.1 | 0.1914 | 0.383 | 0.201 |
| 207 | 266 | 27.4 | 2.66 | 4.8 | 462 | 1.21 | 20.2 | 35.4 | 44.4 | 0.0440 | 0.209 | 0.571 |
| 209 | 282 | 27.0 | 6.30 | 4.5 | 462 | 0.98 | 12.9 | 30.5 | 56.6 | 0.0921 | 0.133 | 0.423 |
| 208 | 284 | 27.0 | 12.00 | 5.4 | 462 | 1.09 | 11.7 | 28.4 | 59.8 | 0.1428 | 0.073 | 0.475 |
| 210 | 268 | 37.6 | 2.11 | 3.5 | 462 | 0.854 | 17.1 | 28.0 | 54.9 | 0.0214 | 0.184 | 0.611 |
| 204* | 292 | 14.6 | 2.67 | 9.5 | 462 | 0.937 | 7.3 | 35.8 | 56.7 | 0.0650 | 0.302 | 0.203 |
| 211 | 282 | 28.3 | 3.35 | 5.3 | 923 | 2.57 | 13.1 | 33.2 | 53.7 | 0.1132 | 0.226 | 0.395 |
| 212** | 289 | 28.4 | 3.21 | 4.0 | 1385 | 3.62 | 11.7 | 33.6 | 54.7 | 0.1556 | 0.248 | 0.348 |

*Air used (13.5% $N_2$ in Feed gas). $C_2H_6$ conversion = 8.0 ± 2.5% based on $N_2$ ratio in and out.
**$CH_3OOH$ = 3.24 g/100 g liquid.
++Traces of esters and acids.

TABLE 2

Analysis of reaction products during the DEO process by on-line injection of product stream.

| Component, mol % $C_2H_6$ free basis | Experiment Number | | | | | |
|---|---|---|---|---|---|---|
| | 207 | 208 | 209 | 210 | 211 | 212 |
| (A) $CH_4$ | Trace | 2.43 | Trace | Trace | Trace | Trace |
| CO | 13.17 | 13.12 | 18.80 | 13.16 | 19.88 | 20.35 |
| $CO_2$ | 5.85 | 5.08 | 7.71 | 7.02 | 8.29 | 6.40 |
| $H_2O$ | 25.37 | 47.09 | 25.30 | 28.07 | 24.30 | 21.51 |
| $CH_3OH$ | 35.12 | 21.90 | 35.66 | 28.95 | 32.04 | 37.21 |
| $C_2H_5OH$ | 20.49 | 10.38 | 12.53 | 22.80 | 15.49 | 14.53 |
| $C_2H_5OH/CH_3OH$ mol/mol | 0.583 | 0.474 | 0.351 | 0.788 | 0.483 | 0.391 |
| Total alcohol selectivity mol % | 55.61 | 32.38 | 48.19 | 51.75 | 56.35 | 51.74 |
| Total alcohol selectivity in carbon products mol % | 74.51 | 63.95 | 64.51 | 71.94 | 66.67 | 65.92 |
| Ethanol selectivity in carbon products mol % | 27.46 | 20.56 | 16.77 | 31.70 | 20.46 | 18.51 |

TABLE 3

Effect of Pressure on Ethanol/Methanol Ratio.
$[O_2] \simeq 3\%$
Conversion Between 5–6 mol %.
Flow Rate 100 mL/min (NTP).

| Pressure atm | T °C. | Selectivity (total alcohol) mol % - carbon | $C_2H_5OH$ $CH_3OH$ (mol/mol) |
|---|---|---|---|
| 15 | 284 | 70 | 0.300 |
| 27 | 266 | 74 | 0.571 |
| 37 | 268 | 72 | 0.788 |
| 66 | 240 | 76 | 3.100 |
| 77 | 238 | 78 | 4.7 |
| 91 | 236 | 80 | 5.9 |

TABLE 4

Effect of Pre-Reactor and Reactor Temperature on the Ethanol/Methanol Ratio

| Exp. No. | $T_R$ °C. | $T_{PR}$ °C. | Flow Rate mL/mm (NTP) | Ethanol/Methanol |
|---|---|---|---|---|
| (A) | Pressure = 100 atm | | $[O_2]$ = 2% | |
| | Reactor Vol. = 4.2 mL | | Reactor length = 15 cm (R) | |
| | Pre-reactor Vol. = 4.2 ml | | Pre-reactor length = 15 cm (PR) | |
| 20.3 | 306 | 249 | 19 | approx 8 |
| 20.4 | 312 | 253 | 18 | 4.5 |
| 20.5 | 332 | 258 | 25 | 4.1 |
| (B) | Reactor Vol. = 14.3 mL | | Reactor length = 15 cm (R) | |
| | Pre-reactor Vol. = 14.3 mL | | Pre-reactor length = 15 cm (PR) | |
| 22.2 | 235 | 194 | 20 | 2.5 |
| 22.3 | 237 | 247 | 18 | 4.0 |
| 22.4 | 239 | 253 | 18 | 2.1 |

We claim:

1. A process for converting ethane into ethanol and methanol, having an ethanol/methanol ratio of about 2.1/1 to about 8/1; which comprises:
    (a) intimately mixing ethane with from 2–15% by volume oxygen,
    (b) pre-heating said mixture in an induction zone to a temperature of about 150° C. to about 400° C. for an induction period of about 10 to about 1500 seconds;
    (c) feeding the resulting pre-heated gas mixture to a lined steel reactor at a pressure within the range of about 10 to about 150 atm, said reactor having an internal surface surrounding a zone in which said gases react, said internal surface being made of a material selected from the group consisting of glass, non-reactive plastics, non-reactive waxes and non-reactive salts; and
    (d) reacting said gases in said reactor at a temperature of about 200° C. to about 350° C. for a time of about 10 seconds to about 2000 seconds in the absence in said reaction of any added material which measurably affects the rate of selectivity of the reaction or the yield of the product.

2. The process of claim 1 wherein the internal surface of said induction zone is made of polytetrafluoroethylene or of glass.

3. The process of claim 1 wherein the internal surface of said reactor is made of polytetrafluoroethylene or of glass.

* * * * *